(12) United States Patent
Froimowitz et al.

(10) Patent No.: US 6,262,064 B1
(45) Date of Patent: *Jul. 17, 2001

(54) OCTAHYDROBENZO[F]QUINOLINE-BASED RECEPTOR AGONISTS AND ANTAGONISTS

(75) Inventors: Mark Froimowitz, Newton, MA (US); James N. Jacob, Saunderstown, RI (US)

(73) Assignees: The Board of Governors for Higher Education; The State of Rhode Island and Providence Plantations., both of Providence, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/237,390

(22) Filed: Jan. 26, 1999

Related U.S. Application Data (63) Continuation of application No. 08/666,286, filed on Sep. 26, 1996, now Pat. No. 5,863,928, and a continuation of application No. PCT/US93/11302, filed on Nov. 19, 1993.

(51) Int. Cl.$^7$ .................. A61K 31/473; C07D 221/06; C07D 409/06; A61P 25/18; A61P 25/20

(52) U.S. Cl. ............................. 514/290; 546/101

(58) Field of Search .............. 514/290; 546/101

(56) References Cited

U.S. PATENT DOCUMENTS

| | | | |
|---|---|---|---|
| 4,228,169 | 10/1980 | Johnson et al. | 424/258 |
| 4,341,786 | 7/1982 | DeMarinis et al. | 424/258 |
| 4,405,626 | 9/1983 | Johnson | 424/258 |
| 4,612,316 | 9/1986 | Andersson et al. | 514/290 |
| 4,678,791 | 7/1987 | Napier et al. | 514/290 |
| 5,030,636 | 7/1991 | Imhof et al. | 514/290 |

FOREIGN PATENT DOCUMENTS

| | | |
|---|---|---|
| 0127597 | 3/1984 | (AT) . |
| 0 059 553 | 9/1982 | (EP) . |
| 0 109 039 | 5/1984 | (EP) . |
| 2 138 815 | 10/1984 | (GB) . |
| WO 84/04303 | 11/1984 | (WO) . |

OTHER PUBLICATIONS

Wikstrom, H., et al., "N–Substituted 1,2,3,4,4a,5,6,10b–Octahydrobenzo[f]quinolines and 3–Phenylpiperidines: Effects on Central Dopamine and σ Receptors," *J. Med. Chem.* 30:2169–2174 (1987).

Wikstrom, H., et al., "Monophenolic Octahydrobenzo[f] quinolines: Central Dopamine– and Serotonin–Receptor Stimulating Activity," *J. Med. Chem.* 25: 925–931 (1982).

Cannon, J.G., et al. "Rigid Congeners of Dopamine Based on Octahydrobenzo[f]quinoline: Peripheral and Central Effects," *Journal Medicinal Chemistry* 22(4):341–347 (1979).

Titeler, M. and Seeman, P., "Presynaptically Acting Catecholamines Bind to α$_2$–Adrenoceptors Labelled by $^3$H–Clonidine," *European Journal of Pharmacology* 67:187–192 (1980).

Ilhan, M., et al., "Dopamine Receptor Stimulating and Alpha Adrenoceptor Blocking Actions of trans (CS–265) and cis (CS–263) Isomers of Nonhydroxylated N–Propyl Octahydrobenzo[f]quinoline," *The Journal of Pharmacology and Experimental Therapeutics* 231(2):361–366 (1984).

Van de Waterbeemd, H., et al., "Quantitative Structure—Activity Relationships and Eudismic Analyses of the Presynaptic Dopaminergic Activity and Dopamine D2 and σ Receptor Affinities of 3–(3–Hydroxyphenyl)piperidines and Octahydrobenzo[f]– quinolines," *J. Med. Chem.* 30:2175–2181 (1987).

Cannon, J.G., et al., "Conformationally Restricted Congeners of Dopamine Derived from Octahydrobenzo[g]quinoline and Octahydrobenzo[f]quinoline," *J. Med. Chem.* 27:190–195 (1984).

Cannon, J.G., et al., "Centrally Acting Emetics. 10. Rigid Dopamine Congeners Derived from Octahydrobenzo[f] quinoline," *Journal of Medicinal Chemistry* 19(8):987–993 (1976).

Cannon, J.G., et al., "cis– and trans–4–n–Propyl–1,2,3,4,4a, 5,6,10b–Octahydrobenzo[f]quinolines," *Journal of Pharmaceutical Sciences* 74(6):672–675 (1985).

Cannon, J.G., et al., "p–Dimethoxy–Substituted trans–Octahydrobenzo[f]– and [g]quinolines: Synthesis and Assessment of Dopaminergic Agonist Effects," *J. Med. Chem.* 29:2529–2534 (1986).

Van Oene, J.C., et al., "trans–N–n–Propyl–7–Hydroxy–Octahydrobenzo(f)Quinoline, A Rigid 3–PPP Analogue with Greater Potency but Lack of Selectivity for Dopamine Autoreceptors," *European Journal of Pharmacology* 87:491–495 (1983).

(List continued on next page.)

*Primary Examiner*—Evelyn Mei Huang
(74) *Attorney, Agent, or Firm*—Hamilton, Brook, Smith & Reynolds, P.C.

(57) ABSTRACT

The present invention relates to a composition, and method of use, of an actahydrobenzo[f]quinoline-based compound represented by the following structural formula:

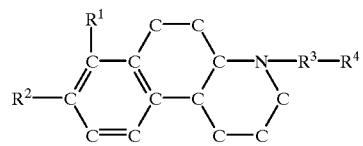

In this formula, $R^1$ is —OH or —OCH$_3$ and $R^2$ is —H, —OH or —OCH$_3$. In addition, $R^3$ is a C1 to C2 saturated or unsaturated, alkyl group. Furthermore, $R^4$ is an aryl group, wherein examples of suitable aryl groups, as defined herein, include phenyl and thienyl groups. The method of this invention relates to the use of the claimed composition to treat psychotic disorders, to treat Parkinson's disease, or to sedate a mammal by administering an effective amount of a claimed composition.

6 Claims, 2 Drawing Sheets

OTHER PUBLICATIONS

Maixner, W., et al., "Pharmacological Effects of 2–Aminotetralins, Octahydrobenzo[f]Quinolines and Clonidine on the Isolated Guinea Pig Ileum," *European Journal of Pharmacology* 71:475–482 (1981).

Kocjan, D. and Hadzi, D., "Conformationally Restricted Dopamine Congeners—A Molecular Mechanics–Based Study," *J. Pharm. Pharmacol.* 35:780–785 (1983).

Sokoloff, P., et al., "Molecular cloning and characterization of a novel dopamine receptor ($D_3$) as a target for neuroleptics," *Nature* 347:146–151 (1990).

Caine, S.B., et al., "Modulation of Cocaine Self–Administration in the Rat Through D–3 Dopamine Receptors," *Science* 260: 1814–1816 (1993).

Seeman, P., et al., "Dopamine D4 receptors elevated in schizophrenia," *Nature* 365:441–445 (1993).

Van Tol, H.H.M., et al., "Cloning of the gene for a human dopamine D4 receptor with high affinity for the antipsychotic clozapine," *Nature* 350:610–614 (1991).

Kaiser, C. and Jain, T., "Dopamine Receptors: Functions, Subtypes and Emerging Concepts," *Medicinal Research Reviews* 5:145–211 (1985).

Manallack, D.T. and Beart P.M., "A Three Dimensional Receptor Model of the Dopamine D2 Receptor from Computer Graphic Analyses of D2 Agonists," *J. Pharm. Pharmacol.* 40:422–428 (1988).

Bradbury, A.J., et al., "A Comparison of Dopamine Agonist Action to Inhibit Locomotor Activity and to Induce Stereotyped Behaviour in the Mouse," *European Journal of Pharmacology* 105:33–47 (1984).

Bradbury, A.J., et al., "Inhibition and Facilitation of Motor Responding of the Mouse by Actions of Dopamine Agonists in the Forebrain," *Neuropharmacology* 23(9):1025–1031 (1984).

Berlan, M., et al., "Pharmacological prospects for $\alpha_2$–adrenoceptor antagonist therapy," *TIPS* 13:277–282 (1992).

Froimowitz, M., et al., "Derivatives of Octahydrobenzo(f)quinolines with High Affinity for Dopaminergic Receptors," CPDD 1993 Annual Scientific Meeting Abstracts, May 19, 1993 (abstract).

kaiser C and Jain T. Medical Research Reviews. 5(20 145–229, 1985.*

* cited by examiner

OCTAHYDROBENZO[F]QUINOLINE-BASED RECEPTOR AGONISTS AND ANTAGONISTS

RELATED APPLICATIONS

This application is a continuation of U.S. application Ser. No. 08/666,286, filed on Sep. 26, 1996 U.S. Pat. No. 5,863,928, which is a continuation of PCT/US93/11302, filed on Nov. 19, 1993, the entire teachings of which are incorporated herein by reference.

GOVERNMENT SUPPORT

This invention was made with Government Support under DA 06681, awarded by the National Institute of Health. The Government has certain rights in this invention.

BACKGROUND OF THE INVENTION

Abnormal transmission to receptors in the central nervous system (CNS) have been implicated in wide variety of diseases, such as Parkinson's disease, psychosis, and many others. Currently, many therapies for these diseases are based upon the use of a medicament as an agonist to stimulate a receptor, or as an antagonist to block a receptor. For example, the treatment of psychosis has been associated with medicament antagonism with dopaminergic receptors.

The ability of a medicament to be effective in vivo to effectively interact with CNS receptors depends upon many factors, including the binding affinity of the medicament for a receptor, the medicaments ability to cross the blood-brain barrier, and the selectivity of the medicament for a targeted receptor. For example, to treat psychotic activity a medicament would be a selective antagonist for the D4 dopamine receptor.

To date, many medicaments with good binding affinities for a particular CNS receptor also bind to non-targeted receptors, often resulting in undesirable side-effects. For example, common side-effects of anti-psychotic drugs include extrapyramidal side-effects. Similarly, some atypical anti-psychotic drugs, such as clozapine which is selective for the D4 receptor, have not exhibited extrapyramidal side-effects but have had severe effects upon the patient's white blood cells, such as agranulocytosis.

Consequently, compositions are needed that can cross the blood-brain barrier to act in vivo and selectively target a CNS receptor without causing severe extrapyramidal side-effects, agranulocytosis or other side-effects associated with current medicaments.

SUMMARY OF THE INVENTION

The present invention relates to a composition, and method of use, of an octahydrobenzo[f]quinoline-based compound represented by the following structural formula:

In this formula, $R^1$ is —OH or —OCH$_3$ and $R^2$ is —H, —OH or —OCH$_3$. In addition, $R^3$ is a C1 to C4 alkyl group. Furthermore, $R^4$ is an aryl group, wherein examples of suitable aryl groups, as defined herein, include phenyl and thienyl groups.

The method of this invention relates to the use of the claimed compositions to treat psychotic disorders, to treat Parkinson's disease, or to sedate a mammal by administering an effective amount of a claimed composition.

The benefits of this invention include the ability to treat psychotic disorders without causing extrapyramidal side-effects or agranulocytosis associated with other antipsychotic medicaments.

DETAILED DESCRIPTION OF THE INVENTION

The features and other details of the invention, either as steps of the invention or as combinations of parts of the invention, will now be more particularly described and pointed out in the claims. It will be understood that the particular embodiments of the invention are shown by way of illustration and not as limitations of the invention. The principle features of this invention can be employed in various embodiments without departing from the scope of the invention.

The present invention relates to a composition, and method of use, of an octahydrobenzo[f]quinoline-based compound which is useful as a receptor binding-affinity composition. As defined herein, a receptor binding-affinity composition is a composition with a binding affinity for a receptor, wherein said composition can act as an agonist, an antagonist or a mixed agonist/antagonist to the receptor. Examples of receptors, for which the compositions of this invention are useful, include D2, D4, 5HT1, 5HT1A, 5HT2, α1 and α2 receptors.

In one embodiment, the octahydrobenzo[f]quinoline-based receptor binding-affinity composition comprises a composition represented by structural formula I. Structural formula I is as follows:

In this composition, $R^1$ is —OH or —OCH$_3$ and $R^2$ is —H, —OH or —OCH$_3$. In addition, $R^3$ is a C1 to C4 alkyl group, such as an ethyl group. Furthermore, $R^4$ is an aryl group. Examples of suitable aryl groups, as defined herein, include phenyl and thienyl groups.

In another embodiment, the receptor binding-affinity composition has a significant affinity to bind to α1-adrenergic, α2-adrenergic and D2 dopamine receptors. This receptor binding-affinity composition is represented by structural formula II. Structural formula II is as follows:

wherein, $R^2$ is —H or —OH, $R^3$ is a C1 to C4 alkyl group; and $R^4$ is an aryl group. The binding affinities of the receptor binding-affinity compositions of this invention for the α1, α2 and D2 receptors are further described in Examples 16–18.

In an additional embodiment, the receptor binding-affinity compositions are dopamine receptor agonists which are effective agonists Parkinson's disease. Receptor binding-affinity compositions suitable to act as dopamine receptor agonists include the trans-enantiomers of dihydroxy compositions represented by structural formula II, such as trans-7,8-dihydroxy-4-phenethyl-1,2,3,4a,5,6,10b-octahydrobenzo[f]quinoline and trans-7,8-dihydroxy-4-thienylethyl-1,2,3,4a,5,6,10b-octahydrobenzo[f]quinoline. Dopamine receptor binding with an agonist results in stereotypic activity. Description of the stereotypic effects of receptor binding-affinity compositions of this invention are provided in Example 25. Details of the evaluation of receptor binding-affinity compositions, as dopamine agonists or antagonists, are provided in Examples 25 and 28.

In yet another embodiment, the receptor binding-affinity compositions produce a sedative effect. Receptor binding-affinity compositions suitable to produce a sedative effect are represented by structural formula II. A sedative effect will result in a reduction in locomotor activity. Description of the sedative effect of receptor binding-affinity compositions of this invention is provided in Example 24. In a preferred embodiment, the sedative compositions include trans-7,8-dihydroxy-4-phenethyl-1,2,3,4a,5,6,10b-octahydrobenzo[f]quinoline and cis-7,8-dihydroxy-4-phenethyl-1,2,3,4a,5,6,10b-octahydrobenzo[f]quinoline.

In yet another embodiment, the receptor binding-affinity compositions are D2 and/or for D4 agonists, or mixed agonists/antagonists, and therefore have an anti-psychotic effect. Suitable anti-psychotic compositions include the cis-enantiomers of the composition represented by structural formula II, and also the trans-enantiomers of the monohydroxy compositions of structural formula II.

In a preferred embodiment, the receptor binding-affinity composition in a preferentially selective antagonist for the D4 receptor over the D2 receptor. D4 selective antagonists have less extrapyramidal side-effects than do non-selective dopamine antagonists. Receptor binding-affinity compositions suitable for D4 selectively include cis-enantiomers of compounds represented by structural formula II. In a particularly preferred embodiment, the D4 selective receptor binding-affinity composition comprises cis-7,8-dihydroxy-4-phenethyl-1,2,3,4a,5,6,10b-octahydrobenzo[f]quinoline. Further description of receptor binding-affinity compositions selectively as an antagonist, or mixed agonist/antagonist, for D4 over D2 is provided in Examples 26 and 27.

In yet another embodiment, receptor binding-affinity compositions of this invention are suitable to selectively bind with 5HT1, 5HT1A and/or 5HT2 serotonin receptors. Examples of receptor binding-affinity compositions suitable to bind with the 5HT1 receptor include trans-7,8-dihydroxy-4-phenethyl-1,2,3,4a,5,6,10b-octahydrobenzo[f]quinoline and trans-(−)-7-hydroxy-4-phenethyl-1,2,3,4a,5,6,10b-octahydrobenzo[f]quinoline.

Receptor binding-affinity compositions suitable to bind with the 5HT1 receptor include trans-(−)-7,8-dihydroxy-4-phenethyl-1,2,3,4a,5,6,10b-octahydrobenzo[f]quinoline, trans-(−)-7-hydroxy-4-phenethyl-1,2,3,4a,5,6,10b-octahydrobenzo[f]quinoline, trans-7,8-dihydroxy-4-thienylethyl-1,2,3,4a,5,6,10b-octahydrobenzo[f]quinoline, and trans-7-hydroxy-4-thienylethyl-1,2,3,4a,5,6,10b-octahydrobenzo-[f]quinoline.

In addition, receptor binding-affinity compositions suitable to bind with the 5HT1 receptor include trans-(−)-7,8-dihydroxy-4-phenethyl-1,2,3,4a,5,6,10b-octahydroxobenzo[f]quinoline, trans-(−)-7-hydroxy-4-phenethyl-1,2,3,4a,5,6,10b-octahydrobenzo[f]quinoline, trans-7-hydroxy-4-phenethyl-1,2,3,4a,5,6,10b-octahydrobenzo [f]quinoline, trans-7,8-dihydroxy-4-thienylethyl-1,2,3,4a,5,6,10b-octahydrobenzo [f]quinoline, and trans-7-hydroxy-4-thienylethyl-1,2,3,4a,5,6,10b-octahydrobenzo [f]quinoline.

In the method for synthesizing the receptor binding-affinity composition of this invention, mono- or di-methoxy-4-arylalkyl-1,2,3,4,4a,5,6,10b-octahydrobenzo [f]quinoline (hereinafter "arylalkyl-OHBQ") is contacted under an inert gas, such as nitrogen or argon, with an agent suitable to convert a methoxy group into a hydroxyl group. Examples of suitable agents include acids and boron tribromide.

In one embodiment of the method of synthesis, mono- or di-methoxy-4-phenylalkyl-1,2,3,4,4a,5,6,10b-octahydrobenzo [f]quinoline (hereinafter "phenylalkyl-OHBQ") is connected under an inert gas, such as nitrogen or argon, with a suitable amount of an acid, preferably HBr, over a combination of time and temperature suitable to convert a methoxy group into a hydroxyl group. Suitable proportions of reagents are about 17 mL to about 35 mL of approximately 48% acid, such as HBR, per mmole of phenylalkyl-OHBQ. It is understood that the volume of acid used can vary approximately proportionally with changes in the concentration of the acid. The preferred ratio of acid to phenylalkyl-OHBQ is about 25 mL to about 30 mL acid per mole of phenylalkyl-OHBQ. A suitable combination of time and temperature is about 1–6 hours at about 100 to 150° C. Suitable phenylalkyl-OHBQ compounds can be synthesized as described in Examples 1, 2 and 8, or as is known in the art.

In another embodiment, mono- or di-methoxy-4-[2-(2-thineyl) alkyl-1,2,3,4,4a,5,6,10b-octahydrobenzo [f]quinoline (hereinafter "thienylalkyl-OHBQ") is contacted under an inert gas, such as nitrogen or argon, with a suitable amount of boron tribromide to convert a methoxy group into a hydroxyl group. Suitable proportions of reagents are about 2 to 4 mmoles of boron tribromide per mmole of thienylalkyl-OHBQ. The preferred ratio of boron tribromide to thienylalkyl-OHBQ is about 3 mmole boron tribromide per mmole thienylalkyl-OHBQ. Suitable thienylalkyl-OHBQ compounds can be synthesized as described in Examples 14 and 15.

The syntheses of compositions of this invention are further described in Examples 3–15.

The method of this invention relates to the use of the receptor binding-affinity compositions claimed. In one embodiment, the method of use comprises a method for treating psychotic disorders, such as schizophrenia, by administering an effective amount of a cis-enantiomer of the compositions represented by structural formula II or a trans-enantiomer of a monohydroxy composition of structural formula II. In a preferred embodiment, an effective amount of cis-7,8-dihydroxy-4-phenethyl-1,2,3,4,4a,5,6,10b-octahydrobenzo [f]quinoline is administered.

In another embodiment, the method of use is a method for sedating a mammal comprising administering an effective amount of a composition represented by structural formula II. In a preferred embodiment, the cis and/or trans enantiomers of 8-dihydroxy-4-phenethyl-1,2,3,4,4a,5,6,10b-octahydrobenzo [f]quinoline are administered.

In yet another embodiment, the method use is a method for treating Parkinson's disease, comprising administering an effective amount of trans-enantiomers of a dihydroxy composition represented by structural formula II. In a preferred embodiment, the composition administered is trans-7,8-dihydroxy-4-phenethyl-1,2,3,4,4a,5,6,10b.

The receptor binding-affinity compositions of this invention, as well as the pharmaceutically acceptable salts, can be used as medicaments, for example, orally, rectally or parentally. Oral administration can be in various forms, such as tablets, coated tablets, dragees, hard and soft gelation capsules, solutions, emulsions or suspensions. Rectal administration can include, for example, suppositories. Parental administration can include, for example, intramuscular, intravenous or subcutaneous injection of solutions, syrups, suspensions, etc.

The pharmaceutical composition, containing the receptor binding-affinity composition, can also include pharmaceutically inert organic or inorganic excipients, such as lactose, corn starch, talc, stearic acid, vegetable oils, waxes, fats, sugars, and the like.

Moreover, these pharmaceutical preparations can contain preserving agents, solubilizing agents, viscosity-increasing substances, stabilizing agents, wetting agents, emulsifying agents, sweetening agents, coloring agents, flavoring agents, salts for varying osmotic pressure, buffers, coating agents or antioxidants. They can also contain or be mixed with other therapeutic agents.

It is also to be understood that the compositions of this invention can be administered in the form of a pro-drug such that upon metabolizing in vivo, the therapeutically effective composition will be formed. For example, 7,8-dimethoxy-4-phenethyl-1,2,4a,5,6,10b-octahydrobenzo [F]quinoline can be administered as a pro-drug which then metabolizes to form 7,8-dihydroxy-4-phenethyl-1,2,3,4a,5,6,10b-octahydrobenzo [f]quinoline.

The dosage administered can vary within wide limits and will depend upon the individual requirements in each particular case. In general, for oral administration a dose of about 1–500 mg/day or for parenteral administration a dose of about 0.1–50 mg/day, dispensed in one or more individual doses, should be sufficient.

Exemplification
Syntheses

EXAMPLE 1

Synthesis of 7,8-Dimethoxy-1,4,5,6-tetrahydrobenzo [f]quinoline3 (2H)-one

A mixture of (20 g, 0.0961 mole) of 2,3-dimethoxycinnannic acid in 120 mL of $CHCl_3$ and 200 mL of EtOH was hydrogenated at 30 psig in the presence of 2.0 g of 10% Pd/C catalyst to form ethyl-3-(2,3-dimethoxyphenyl) propionate (hereinafter, "Compound 1"). The catalyst was removed by filtration and the filtrate was evaporated under reduced pressure. The residue was distillated under reduced pressure to give 22 g (96% yield) of liquid with a boiling point of 143° C./1.15 mmHg. Elemental analysis gave $C_{13}H_{18}O_4$ (C,H,N).

Sodium hydride (13.75 g in a 60% dispersion in mineral oil) was washed three times with hexanes. The flask, containing the sodium hydride, was evacuated until no hexanes were detectable and then the sodium hydride was placed under $N_2$ by evacuating and filling the flask with $N_2$ several times. Dimethyl sulfoxide (200 mL) were introduced via dropping funnel and the mixture was heated with stirring to 70–75° C. until the evolution of hydrogen ceased. The reaction mixture was cooled in an ice bath and 175 ml of dry THF was added via dropping funnel. After 15 minutes, 40.95 g (0.1719 mole) of Compound 1 was added to the cooled flask over a period of 10 minutes. The ice bath was removed and stirring was continued for 2.5 hours, whereby 2-(2,3-dimethoxyphenyl)-ethylmethylsulfinyl methylketone (hereinafter, "Compound 2") was formed. The reaction mixture was then poured into 700 mL of ice, acidified with 6N HCl to pH3–4 and thoroughly extracted with dichloromethane. The combined extracts were washed three times with water, dried over $Na_2SO_4$, and evaporated by reduced pressure to afford an oil which solidified upon trituration with diisopropyl ether in an ice bath. This solid was collected on a filter and washed with cold $Et_2O$ to afford 42 g (90% yield) of white powder with a melting point at 55–56° C. Compound 2 is cited by J. G. Cannon et al., *J. Med. Chem.*, 20(9):1111 (1977) as having a melting point of 55.5–56.5° C.

Compound 2 (21.6 g (0.0799 mole)) and 18 g of trifluoroacetic acid were refluxed in 860 mL of benzene for 1.5 hours. The cooled reaction mixture was washed with 5% $Na_2CO_3$ and volatiles were removed under reduced pressure to leave 21 g of oil, comprising 3,4-dihydro-1-methylthio-5,6-dimethoxy-2(1H)-naphthalenone, (hereinafter, "Compound 3") which was then utilized without further purification.

Compound 3 (7.2 g (0.0285 mole)) in 75 mL of glacial acetic acid was hydrogenated in the presence of 4.6 g of 5% Pd/C catalyst at 30 psi and at room temperature for 48 hours. The catalyst was removed by filtration and the filtrate was evaporated at reduced pressure to leave a heavy oil which was shaken vigorously with a solution of 20.5 g of $NaHSO_4$, in 42 mL of $H_2O$ and 12.6 mL of EtOH. The bisulfite addition product was collected, washed with EtOH/$Et_2O$ and then dried. A yield of 4.08 g of bisulfite addition product was obtained.

3,4-Dihydro-5,6-dimethoxy-2(1H)-naphthalenone (hereinafter, "Compound 4") was obtained by treating the bisulfite addition compound with excess 10% $Na_2CO_3$ and extracting the resulting mixture with benzene. The extract was washed with 10% HCl and then with water and subsequently dried over $Na_2SO_4$. Volatiles were removed under reduced pressure to leave a residue which was crystallized from cyclohexane to afford 2.61 g (45% yield) of white needles with melting point of 62° C. J. G. Cannon et al., *J. Med. Chem.*, 20(9):111 (1977) cites Compound 4 as having a melting point range of 61–64° C.

To a solution, of 11.83 g (0.0579 mole) of Compound 4 and 0.07 g of p-toluenesulfonic acid in 92 mL of benzene, was added 5.77 g of pyrolidine. The mixture was heated under $N_2$ and refluxed in a Dean-Stark water separation apparatus for 3 hours. The volatiles were removed at reduced pressure to leave a brown oil. Acrylamide (15.23 g (0.2143 mole)) was added to the oil and the mixture was heated at 80° C. for 2 hours then at 130° C. for 30 minutes. The reaction mixture was then diluted with 85 mL of hot water and acidified to ph 3–4 with 6N HCl. The resulting precipitate, which essentially consisted of 7,8-dimethoxy-1,4,5,6-tetrahydrobenzo[f]-quinoline-3 (2H)-one (hereinafter, "Compound 5") was collected on a filter and triturated with 164 mL of Et$_2$0, to leave a white powder, which was recrystallized from Me$_2$CO to give 10.63 g (70% yield) of white crystals with a melting point of 231–231° C. (J. G. Cannon et al., *J. Med. Chem*, 19 (8):992 (1976)) cites Compound 5 as having a melting point range of 233–236° C.

EXAMPLE 2

Synthesis of Trans-7,8-Dimethoxy-4-Phenethyl-1,2, 3,4,4a,5,6,10b-Octahydrobenzo[f]Quinoline Triethylsilane (13.45 g (0.1157 mole)) was added to a solution of 5.0 g (0.0193 mole) of Compound 5 in 50 mL of dichloromethane. The resulting mixture was stirred for 10 minutes at room temperature and then 30 mL of trifluoroacetic acid was added while cooling in an ice bath. The resulting mixture was stirred at room temperature of 27 hours. Volatiles were evaporated under reduced pressure. The crude mixture recrystallized with Me$_2$CO to give 4.19 g (81% yield) of white crystal trans-7,8-Dimethoxy-1,4,4a, 5,6,10b-hexahydro-benzo[f]quinoline-3 (2H)-one (hereinafter, "trans-6"). Melting point 239–240° C. Cannon, et al., *Synthesis*, 494 (1986) cites trans-6 as having a melting point range of 232–233° C. (ether). $^1$H NMR (CDCl$_3$) shifts observed were 1.64–1.85 (m,2H aliph); 1.99–2.07 (m,1H aliph); 2.53–2.85 (m,5H aliph); 3.05–3.14 (q,1H aliph), 3.27–3.36 (m,1H aliph); 3.82, 3.86 (2s,6H,OCH$_3$); 5.91 (S,1H,NH); 6.82, 7.00 (2d,2H,ArH).

To a stirred solution of 3.49 g of LiAlH$_4$ in 60 mL of THF was added 4.0 g (0.0153 mole) of trans-6 in 80 mL of THF. The resulting mixture was stirred at room temperature, cooled and quenched with 20 mL of water and 10 mL of 20% NaOH. The resulting mixture was extracted with 350 mL of ether. The extract was dried with Na$_2$SO$_4$ and evaporated to leave 3.79 g of almost pure oil. On keeping, the trans-7,8-Dimethoxy-1,2,3,4,4a,5,6,10b-octahydrobenzo[f]quinoline (hereinafter, "trans-7") solidified. Solidified trans-7 was utilized in the next step without purification. The $^1$H NMR (CDCl$_3$) shifts observed were 1.24–1.29 (m,1H aliph); 1.66–1.98 (m,4H aliph); 2.26 (s,2H, NH ½ H$_2$O); 2.38–2.51 (m,3H aliph); 2.69–2.79 (m,2H aliph); 3.00–3.19 (m,2H aliph); 3.80, 3.84 (2S,6H,OCH$_3$); 6.78, 6.98 (2d,2H,ArH).

Sodium borohydride (0.80 g) was added in small portion to a solution of 9.74 g (0.0715 mole) of phenylacetic acid in 60 mL of dry benzene, while maintaining temperature below 20° C. When hydrogen evolution ceased (about 6 hours), 1.10 g (0.0042 mole) of trans-7, in 20 mL of benzene, was added and the resulting mixture was refluxed overnight. The cooled mixture was shaken with excess 2N NaOH. The organic layer was dried with Na$_2$SO$_4$ and evaporated. The residue was recrystallized from EtOH to give 1.05 g (71% yield) of white solid trans-7,8-Dimethoxy-(phenethyl-1,2,3, 4,4a,–5,6,10b- octahydrobenzo[f]quinoline (hereinafter, "trans-8"). Melting point 110–111° C. The $^1$H NMR (CDCl$_3$) shifts observed were 1.17, 3.13 (m,16H,—CH$_2$—, >CH—), 3.81, 3.85 (2S,6H OCH$_3$), 6.76–7.33 (m,7H, ArH). Elemental analysis gave C$_{23}$H$_{29}$NO$_2$ (C,H,N).

EXAMPLE 3

Synthesis of Trans-7,8-Dihydroxy-4-Phenethyl-1,2, 3,4,4a,5,6,10b-Octahydrobenzo[f]Quinoline Trans-8 (0.39 g 0.0011 mole)) was heated under N$_2$ with 30 mL of 48% HBr at 135° C. for 3 hours. The volatiles were evaporated under reduced pressure and the residue was recrystallized from MeOH to give 0.33 g (73% yield) of trans-7,8-dihydroxy-4-phenethyl-1,2,3,4,4a,–5,6,10b-octahydrobenzo[f]quinoline (hereinafter, "trans-9) as a hydrobromide. Melting point 252–3° C. Elemental analysis gave C$_{21}$H$_{26}$NO$_2$.¼H$_2$O (C,H,N).

EXAMPLE 4

Separation of Isomers of Trans-7,8-Dimethoxy-4-Phenethyl-1,2,3,4,4a,5,6,10b-Octahydrobenzo[f] Quinoline Trans-8 (94 mg) was dissolved in 1.5 mL of EtOH. This solution (200 µL) was applied to a J. T. Baker semipreparative HPLC column (chiralcel OD, J. T. Baker Inc. 10 mm inner diameter, mobile phase: EtOH) using a flow rate of 1.7 mL/minute. Seven fractions were collected, using UV detection to indicate the start of sample collection. Fractions 1 and 2 were pooled from consecutive runs and gave after solvent removal the solid (+)-isomer of trans-8 (hereinafter, "trans-(+)-8") with [α]$_D$ (20° C.) of +89.9 (c 0.28, MeOH).

The seventh fractions were pooled from consecutive runs and gave after solvent removal 40 mg of the solid (–)-isomer of trans-8 (hereinafter, "trans-(–)-8") with [α]$_D$ (20° C.) of –89.4 (c 0.16, MeOH).

EXAMPLE 5

Synthesis of Trans-(+)-7,8-Dihydroxy-4-Phenethyl-1,2,3,4,4a,5,6,10b-Octahydrobenzo[f]Quinoline Trans-(+)7,8-dihydroxy-4-phenethyl-1,2,3,4,4a,5,6, 10b-octahydrobenzo[f]quinoline (hereinafter, "trans-(+)-9") was prepared in 74% yield from 40 mg (0.11 mmole) of trans-(+)-8 by the method described for trans-9 as described in Example 3. The melting point observed was 253–4° C. (dec.) and [α]$_D$ (20° C.) was +74.6 (c 0.17, MeOH).

EXAMPLE 6

Synthesis of Trans-(–)-7.8-Dihydroxy-4-Phenethyl-1,2,3,4,4a,5,6,10b-Octahydrobenzo[f]Quinoline Trans-(–)-7,8-Dihydroxy-4-phenethyl-1,2,3,4,4a,5,6, 10b-octahydrobenzo[f]quinoline (hereinafter, "trans-(–)-9") was prepared in 72% yield from 40 mg (0.11 mole) of trans-(–)-8 by the method described for trans-9 in Example 3. The melting point observed was 253–4° C. (dec.) and [α]$_D$ (20° C.) was –68.0 (c 0.25, MeOH).

EXAMPLE 7

Synthesis of cis-7,8-Dihydroxy-4-Phenethyl-1,2,3,4, 4a,5,6,10b-Octahydrobenzo[f]Quinoline Compound 5 (1.3 g (0.0050 mole)) in 86 mL of glacial acetic acid was hydrogenated at 28 psi in the presence of 0.6 g of 10% Pd/C catalyst for 4 hours to form cis-7,8-dimethoxy-1,4,4a,5,6,10b-hexahydrobenzo[f]quinoline-3 (2H)-one (hereinafter, "cis-6"). The catalyst was removed by filtration and the filtrate was evaporated under reduced pressure. The residue was taken up in 2N NaOH and the resulting solution was extracted with CH$_2$Cl$_2$. The extracts were dried with Na$_2$SO$_4$ and evaporated to give a solid, which was recrystallized from Me$_2$CO to give 0.93 g (71% yield) with a melting point of 174–5° C. Elemental analysis gave C$_{15}$H$_{19}$NO$_3$ (C,H,N).

Cis-7,8-dimethoxy-1,2,3,4,4a,5,6,10b-octahydrobenzo[f] quinoline (hereinafter, "cis-7") was prepared in 88% yield;

from 0.58 g (2.22 mmole) of cis-6 by the method described to form trans-7 in Example 2. The melting point was 252–4° C. (B.HCl). Cis-7 is cited by J. G. Cannon et al., *J. Med. Chem.*, 22(4):341 (1979) as having a melting point of 243–5° C. (B.HCl). The $_1$H NMR (CDCl$_3$) shifts observed were 1.56–3.30 (m,12H,aliph.); 3.81; 3.85 (2s,6H, OCH$_3$); 6.77–6.92 (2d,2H,ArH).

Cis-7,8-dimethoxy-4-phenethyl-1,2,3,4,4a,5,6,10b-octahydrobenzo-[f]quinoline (hereinafter, "cis-8") was prepared from cis-7 using the method described to form trans-8 in Example 2. The melting point was 75–76° C. $^1$H NMR (CDCl$_3$) shifts observed were 1.61–1.71 (m,2H); 1.76–2.01 (m,4H), 2.51–2.62(m,2H); 2.72–2.76 (m,1H); 2.81–2.87 (t,4H); 2.93–3.21 (m,3H); 3.81, 3.85 (2s,6H, OCH$_3$); 6.78 (d,1H,ArH); 6.86 (d,1H,ArH); 7.21–7.34 (m,5H,ArH). Elemental analysis (hydrochloride) gave C$_{23}$H$_{30}$ClNO$_2$.¼H$_2$O (C,H,N).

Cis-7,8-Dihydroxy-4-phenethyl-1,2,3,4,4a,5,6,10-octahydrobenzo-[f]quinoline (hereinafter, "cis-9") was prepared from cis-8 by the method described to form trans-9 in Example 3. The melting point observed was 241–2° C. and [α]$_D$ (20° C.) was 1.66 (c 0.18, MeOH).

The (+) and (–)-isomers of cis-9 were then formed from cis-8 by the methods described in Examples 4–6 for forming the (+) and (–)-isomers of trans-9.

EXAMPLE 8

Synthesis of Trans-7-Hydroxy-4-phenethyl-1,2,3,4, 4a,5,6,10b-Octahydrobenzo[f]Quinoline 1.6-Dihydroxynapthalene (44 g (0.247 mole)) was mixed with 245 mL of 2N NaOH and 55 mL of methyl sulfate. The mixture was stirred at room temperature. When the pH of the mixture was 6, 124 mL of 2N NaOH and 26.4 mL of methyl sulfate were added and stirred until 1,6-dihyroxynapthalene was disappeared. Excess of methyl sulfate was destroyed by heating for 30 minutes at 100° C. The warm liquid was acidified and extracted with CH$_2$Cl$_2$. The CH$_2$Cl$_2$ layer was washed twice with 2N NaOH and evaporated. A yield of 47.73 g(92%) of 1,6-dimethoxynaphthanene was obtained. Sodium (19 g) was added to a solution of 22.5 of crude 1,6-dimethoxynaphthalene in 190 mL of boiling ethanol. Ethanol (40 mL) was then added and heating continued under reflux until the Na had disappeared (about 40 minutes). Water (60 mL) was added cautiously and then most of the ethanol was removed under reduced pressure. The residue was mixed with 30 mL of water and the lower aqueous layer was separated and extracted twice with dioxane, which was then combined with the oily upper layer. Water (25 mL) and then hydrochloric acid (density of 1.18 g/mL) until the mixture was acidic (pH 2–3). Then, 3 mL more of HCl was added and the liquid was stirred at about 70° C. for 30 minutes. The lower oily layer was separated, the aqueous layer was diluted with 100 mL of water, separated from more oil, and extracted thrice with methylene chloride. The combined oil and methylene chloride extracts were stirred with 50 mL of saturated aqueous sodium bisulfite until crystallization began. The solid was triturated with ether, then washed with ether and dried. Free 5-methoxy-2-tetralone was obtained by treating the bisulfite addition compound with excess 10% Na$_2$CO$_3$ and extracting the resulting mixture with methylene chloride. The extract was washed with 10% HCl and then with water and dried with Na$_2$SO$_4$. Volatiles were removed under reduced pressure to leave 17 g (81% yield) of liquid. On keeping, the 3,4-Dihydro-5-methoxy-2-(1H)-naphthalenone (hereinafter, "Compound 20") solidified in massive prisms with a melting point of 25–36° C.

7-Methoxy-1,4,5,6-tetrahydrobenzo[f]quinoline-3 (2H)-one (hereinafter, "Compound 21") was prepared from Compound 20 by the method described for synthesizing Compound 5 in Example 1. The $^1$H NMR (CDCl$_3$) shifts observed were 2.32–2.37 (m,2H); 2.62–2.73 (m,4H); 2.88–2.93 (t,2H); 3.83 (5,3H); 6.71–6.78 (q,2H); 7.14–7.19 (t,1H); 7.98 (s,1H,NH).

Trans-7-methoxy-1,4,4a,5,6,10b-hyxahydrobenzo[f] quinolin-3(2H(-one (hereinafter, "trans-22") was prepared from Compound 21 by the method described for synthesizing Compound 6 as described in Example 2. The melting point observed was 274–5° C. The $^1$H NMR (CDCl$_3$) shifts observed were 1.66–1.86 (m,2H); 2.05–2.13 (m,1H); 257–2.77 (m,5H); 2.96–3.04 (q,1H); 3.32–3.40 (m,1H); 3.83 (s,1H); 6.27 (s,1H, NH); 6.74–6.76 (d,1H); 6.92–6.94 (d,1H); 7.15–7.22 (t,1H).

Trans-7-methoxy,1,4,4a,5,6,10b-octahydrobenzo[f] quinoline (hereinafter, "trans-23") was prepared from Compound 22 by the method described for Compound 7 in Example 2. The $^1$H NMR (CLCl$_3$) shifts observed were 1.21–1.34 (m,1H); 1.62–1.78 (m,2H); 1.83–1.95 (m,3H)l 2.41–2.53 (m,3H); 2.59–2.76 (m,2H); 2.93–3.01 (q1H); 3.13–3.16 (m,1H); 3.82 (S,3H); 6.70–6.72 (d,1H); 6.92–6.94 (d,1H); 7.14–7.20 (t,1H).

Trans-7-methoxy-4-phenethyl-1,2,3,4,4a,5,6,10b-octahydrobenzo[f]quinoline (hereinafter, "trans-24") was prepared from trans-23 by the method described for synthesizing Compound 8 as described in Example 2. The $^1$H NMR (CDCl$_3$) shifts observed were 1.17–3.13 (m,16H,aliph.); 3.81 (s,3H,OCH$_3$); 6.68–6.95 (2d,2H,ArH); 7.13–7.32 (m,6H, ArH). Elemental analysis (hydrochloride) gave C$_{22}$H$_{28}$ClNO.¼H$_2$O (C,H,N).

Trans-7-hydroxy-4-phenethyl-1,2,3,4,4a,5,6,10b-octahydrobenzo[f]quinoline (hereinafter, "trans-25") was prepared from 0.25 g (0.78 mole) of trans-24 by the method described for synthesizing trans-9 as described in Example 3.The melting point observed was 284–5° C. Elemental analysis gave C$_{21}$H$_{26}$BrNO.¼H$_2$O (C,H,N).

EXAMPLE 9

Separation of Isomers of Trans-7-Methoxy-4-Phenethyl-1,2,3,4,4a,5,6,10b-Octahydrobenzo[f] Quinoline Trans-24 (218 mg) was dissolved in 4.5 mL of ethanol. Separation was then performed as described to separate trans-(+)-8 and trans-(–)-8 in Example 4. Fractions 1 and 2 were pooled from consecutive runs and gave after solvent removal 100 mg of solid (+-isomer of trans-24 (hereinafter, "trans-(+)-24") with [α]$_D$ (20° C.) of +100.9 (c 0.34, MeOH). Fractions 7 and 8 were pooled from consecutive runs and concentrated, yielding 112 mg of solid (–)-isomer of trans-24 (hereinafter "trans-(–)-24") with [α]$_D$ (20° C.) of –95.2 (c 0.23, MeOH).

The (+) and (–)-isomers of trans-25 were then formed by the method of synthesizing the (+) and (–)-isomers of trans-9 described in Examples 5 and 6.

EXAMPLE 10

Synthesis of cis-7-Hydroxy-4-Phenethyl-1,2,3,4,4a,5,6,10b-Octahydrobenzo[f]Quinoline Cis-7-methoxy,1,4,4a,5,6,10b-octahydrobenzo[f] quinoline (hereinafter, "cis-23") was prepared from Compound 22 by the method described for trans-23 in Example 8.

Cis-7-methoxy-4-phenethyl-1,2,3,4,4a,5,6,10b-octahydrobenzo[f]quinoline (hereinafter, "cis-24") was prepared in 73% yield form 0.67 g (3.08 mmole) of cis-23 by the method described for synthesizing trans-24 as described in Example 8. The melting point observed was 226–7° C. The $^1$H NMR (CDCl$_3$) shifts observed were 1.61–3.24 (m,16H,aliph.); 3.81(s,3H,OCH$_3$); 6.64–6.76 (2.2H, ArH); 7.09–7.32 (m,6H, ArH). Elemental analysis (hydrochloride) gave C$_{22}$H$_{28}$ClNO (C,H,N).

Cis-7-hydroxy-4-phenethyl-1,2,3,4,4a,5,6,10b-octahydrobenzo[f]quinoline (hereinafter, "cis-25") was prepared in 60% yield from 0.25 g (0.78 mole) of cis-24 by the method described for synthesizing trans-25 as described in Example 8. The melting point observed was 261–2° C. Elemental analysis gave C$_{21}$H$_{26}$BrNO (C,H,N).

EXAMPLE 11

Separation of Isomers of cis-7-Methoxy-4-Phenethyl-1,2,3,4,4a,5,6,10b-Octahydrobenzo[f]Quinoline Cis-24 (120 mg) was dissolved in 2.9 mL of ethanol. Separation was then performed as described to separate (+)-trans-8 and (−)-trans-8 in Example 4. Fractions 1 and 2 were pooled from consecutive runs and gave after solvent removal 40 mg of solid (−)-isomer of cis-24 (hereinafter, "cis-(−)-24") with $[\alpha]_D$ (20° C.) of −9.33 (c 0.20, Meoh). Fractions 6 and 7 were pooled from consecutive runs and concentrated, yielding 40 mg of solid (+)-isomer of cis-24 (hereinafter "cis-(+)-24") with $[\alpha]_D$ (20° C.) of +9.57 (c 0.23, MeOH).

EXAMPLE 12

Synthesis of cis-+)-7-Hydroxy-4-Phenethyl-1,2,3,4,4a,5,6,10b-Octahydrobenzo[f]Quinoline Cis-(+)-7-hydroxy-4-phenethyl-1,2,3,4,4a,5,6, 10b-octahydrobenzo[f]quinoline (hereinafter, "cis-(+)-25") was prepared in 50% yield from 37 mg (0.12 mmole) of cis-(+)-24 by the method of forming trans-9 as described in Example 3. The melting point observed was 194° C. and $[\alpha]_D$ (20° C.) was +6.05 (c 0.22, MeOH).

EXAMPLE 13

Synthesis of cis-(−)-7-Hydroxy-4-Phenethyl-1,2,3,4,4a,5,6,10b-Octahydrobenzo[f]Quinoline Cis-(−)-7-hydroxy4-phenethyl-1,2,3,4,4a,5,6, 10b)-octahydrobenzo[f]quinoline (hereinafter, "cis-(−)-25") was prepared in 46% yield from 34 mg (0.11 mmole) of cis-(−-24 by the method described for trans-9 in Example 3. The melting point observed was 196° C. and $[\alpha]_D$ (20° C.) was −6.0 (c 0.20, MeOH).

EXAMPLE 14

Synthesis of Trans-7-hydroxy4-[2-(2-thienyl)ethyl-1,2,3,4,4a,5,6,10b-Octahydro-Benzo[f]Quinoline Hydrobromide To a solution of 75 mg (0.345 mmoles) of trans-7-methoxy-1,2,3,4,4a,5,6,10b-octahydrobenzo[f]quinoline and 98 mg (0.69 mmoles) of 2-thienylacetic acid in 6 mL of xylene, was added 50 mg (0.69 mmoles) of Me$_3$NBH$_3$. The mixture was refluxed under nitrogen for 20 hours. After cooling, the mixture was washed with NaHCO$_3$ solution and then with water. The xylene layer was dried with Na$_2$SO$_4$, filtered and concentrated under reduced pressure. The crude layer was purified by using a silica gel column. The yield of trans-7-methoxy-4-[2-(2-thienyl)ethyl-1,2,3,4,4a,5,6,10b-octahydrobenzo[f]quinoline (hereinafter "trans-30") was 103 mg (91%) The $^1$H NMR (CDCl$_3$) shifts observed were 1.17–3.14 (m,16H, aliph); 3.82 (s,3H,OCH$_3$); 6.70, 6.83 (2d,2H, ArH); 6.92–6.98 (m,2H, ArH); 7.13–7.18 (m,2H, ArH). Elemental analysis results were C$_{20}$H$_{25}$NOS (C,H,N) with 73.35 C 7.70 H 4.28 N predicted and 73.56 C 7.74 H 4.27 N found.

To a stirred solution of 100 mg (0.305 mmole) of trans-30 in 5 mL of CH$_2$Cl$_2$, under nitrogen and at −70° C., were added dropwise 1.04 mL of 1M boron tribromide solution in CH$_2$Cl$_2$. After twenty minutes, the temperature was allowed to increase to room temperature for 1.5 hours, then it was brought to −70° C. and 3 mL of methanol was added dropwise. The temperature was then allowed to rise to 20° C. The solution was concentrated under reduced pressure at room temperature. To the residue, 5 mL of methanol was added and then evaporated under reduced pressure. To the residue, 5 mL of water was added and then the mixture was made alkaline, to a pH of about 8–9, with 10% NaHCO$_3$ and then extracted with CH$_2$Cl$_2$. The CH$_2$Cl$_2$ layer was separated and dried over Na$_2$So$_4$. After filtration, the solvent was evaporated and left an oil which was then purified by silica gel column. The product was dissolved in ethanol and then HBr and Et$_2$O were added to produce 29 mg (24% yield) of trans-7-hydroxy-4-[2-(2-thienyl)ethyl-1,2,3,4,4a,5,6,10b-octahydrobenzo[f]quinoline (hereinafter "trans-31"). Elemental analysis results were C$_{19}$H$_{24}$BrNOS.½H$_2$O (C,H, N) with 56.57 C 6.25 H 3.47 N 7.95 S predicted and 56.95 C 6.01 H 3.04 N 7.81 S found.

EXAMPLE 15

Synthesis of Trans-7,8-dihydroxy-4-[2-(2-Thienyl)Ethyl-1,2,3,4,4a,5,6,10b-Octahydro-Benzo[f]Quinoline Hydrobromide Trans-7,8-dimethoxy-4-[2-2-thienyl)ethyl-1,2,3,4,4a,5,6, 10b-octahydrobenzo[f]quinoline (hereinafter "trans-32") was prepared in 69% yield from 410 mg (1.65 mmole) of trans-2 by the method described for trans-30 in Example 15. The $^1$H NMR (CDCl$_3$) shifts observed were 1.17–3.15 (m,16H, aliph); 3.80, 3.84 (2s,6H,OCH$_3$); 6.76–7.15 (m,5H, ArH). Elemental analysis results were C$_{21}$H$_{27}$NO$_2$S (C,H,N) with 70.55 C 7.61 H 3.92N 8.97S predicted and 70.47C 7.68H 3.91N 8.79S found.

Trans-7,8-dihydroxy-4-[2-(2-thienyl)ethyl-1,2,3,4,4a,5,6, 10b-octahydrobenzo[f]quinoline (hereinafter "trans-33") was prepared in from trans-7,8-dimethoxy-1,2,3,4,4a,5,6, 10b-octahydrobenzo[f]quinoline according to the method of Example 15.

Chemical Analysis

Melting points were determined in open capillary tubes using a Thomas-Hoover Uni-Melt apparatus and are uncorrected. Elemental analyses were performed by Midwest Microlab, Indianapolis, Ind. Where analyses are indicated by the symbols of the elements, the analytical results were within ±0.4% of the theoretical values. $^1$H NMR spectra were obtained on a Varian EM-390 Spectrometer. Chemical shifts are in parts per million with respect to TMS. Optical rotations were obtained with an AUTOPAL 111 Automatic Polarimeter. Silica gel (230–400 mesh) suitable for column chromatographic use was purchased from EM Science, a Division of EM Industries, Inc. Thin layer chromatography was run on precoated (0.2 mm) silica gel 6° F.-254 plates manufactured by EM Science. HPLC was performed with a Waters Model Pump 7125 Injector, and Waters Model 440 Absorbent Detector.

Receptor Binding Analyses

The binding affinities of the compositions of this invention were assayed for various receptors. In these assays, the binding reaction was initiated by the addition of varying concentrations of the potential binding composition and a radioligand to an appropriate tissue. The assay was then incubated to allow binding. Binding was then terminated by dilution of the assay with a cold buffer, followed by rapid vacuum filtration onto Whatman GI/C filters that were presoaked in 0.1% polyethylene imine for at least 3 hours. Radioactivity trapped onto the filters was determined and compared to control values in order to ascertain any interactions of test compounds with the binding sites. Binding affinity analyses were performed by Novascreen, Division of the Adheron Corporation, Hanover, Md.

EXAMPLE 16

Dopamine (D1 and D2) Central Binding Assays

Dopamine (D1) binding assays were performed on rat striatal membranes according to the method described by Billard, et al., *Life Sciences*, 35:1885–1893 (1984). Incubation was conducted in 50 nM HEPES containing 1.0 mM EDTA, 4.0 mM MgSO$_4$, and 10 μM Ketanserin (pH 7.4) at 37° C. for 60 minutes. The radioligand used was [$^3$H]SCH 23390 (70–87 Ci/mmol). The final radioligand concentration was 0.5 nM.

The reference compound and the positive control was SCH 23390. The assay was characterized by a binding affinity ($K_i$) of 0.53 nM, a receptor number ($B_{max}$) of 69 fmol/g wet weight of tissue, and 90% non-specific binding as determined using 1.0 μM SCH 23390.

The values for binding affinity of the reference compounds for dopamine D1 receptors are provided in Table I.

TABLE I

| Compounds | $K_i$ (nM) |
|---|---|
| Spiperone | 0.1 |
| SCH 23390 | 7.7 |
| Butaclamol | 37.3 |
| Metoclopramide | 97.3 |
| SKF 38393 | 127 |

Dopamine (D2) binding assays were performed on rat striatal membranes according to the method described by Imafuku K., *Brain Research*, 402:331–338 (1987). Incubation was conducted in 50 mM TRIS-HCl (pH 7.5) containing 100 mM NaCl at 25° C. for 60 minutes. The radioligand used was [$^3$H]Sulpiride (60–80 Ci/mmol). The final ligand concentration was 0.5 nM.

The reference compound and the positive control was sulpiride. The assay was characterized by a $K_i$ of 3.0 nM, a $B_{max}$ of 348 fmol/g wet weight of tissue, and 90% non-specific binding as determined using 10 μM sulpiride.

The values for binding affinity of the reference compounds for dopamine D2 receptors are provided in Table II.

TABLE II

| Compounds | $K_i$ (nM) |
|---|---|
| Spiperone | 0.1 |
| Butaclamol | 0.7 |
| Sulpiride | 3.4 |
| Metoclopramide | 10.2 |
| SKF 38393 | 475 |
| SCH 23390 | 503 |

The values for dopamine D1 and D2 receptor binding affinities for the compositions of this invention are provided in Table III, as either the $K_i$ (in nM) or for compositions with lesser binding affinities, the percent binding by a concentration of $10^{-5}$. These results show that trans-9, trans-(-)-9, trans-25, trans-(-)-25, trans-31, cis-9, cis-(-)-9, cis-25, and trans-33 demonstrated good dopamine receptor binding affinities and were highly selective for the D2 dopamine receptor over the D1 dopamine receptor. It is also apparent that the selectivities of trans-9, cis-9 and trans-25 for the D2 dopamine receptor are due to the (-)-isomers, as the (+)-isomers have only weak affinities for the D2 receptor.

TABLE III

| COMPOUND | D1 | D2 | 5-HT1 | 5-HT1A | 5-HT2 | 5-HT3 | $\alpha_1$ | $\alpha_2$ | $\beta$ |
|---|---|---|---|---|---|---|---|---|---|
| trans-9 | 3600 | 2.2 | 150 | 51% | 86% | 22% | 80 | 22 | 11% |
| trans-(-)-9 | 3500 | 0.38 | 3300 | 67 | 26 | 21% | 130 | 9.0 | 19% |
| trans-(+)-9 | 13% | 2500 | 52% | 910 | | 23% | 53 | 550 | 3% |
| cis-9 | 22% | 22 | 23% | 26% | 31% | 11% | 190 | 27 | 11% |
| cis-(-)-9 | 15% | 54 | 23% | 43% | 36% | 11% | 180 | 74 | 39% |
| cis-(+)-9 | 5% | 49% | 19% | 10% | 27% | 11% | 66% | 39% | 0% |
| trans-25 | 5100 | 0.87 | 470 | | 27 | | 4.5 | 0.22 | 48% |
| trans-(-)-25 | 3600 | 0.90 | 240 | 11 | 410 | 39% | 4.8 | 2.1 | 47% |
| trans-(+)-25 | 24% | 400 | 59% | 410 | 9.5 | 23% | 5.5 | 440 | 27% |
| cis-25 | 18% | 6.6 | 36% | | 62% | | 16 | 0.27 | 52% |
| trans-33 | 73% | 57 | 1800 | 190 | 100 | 43% | 180 | 19 | 36% |
| trans-31 | 55% | 1.9 | 62% | 36 | 80 | 7% | 17 | 7.2 | 11% |

EXAMPLE 17

Alpha1-Adrenergic (Non-Selective) Binding Assay

Alpha1-adrenergic binding assays were performed on rat forebrain membranes according to the method described by Timmermans, et al., *Molecular Pharmacology*, 20:295–301 (1981).

Incubation was conducted in 50 mM TRIS-HCl (pH 7.7) at 25° C. for 60 minutes. The radioligand used was [$^3$H] Prazosin (70–87 Ci/mmol). The final ligand concentration was 0.5 nm.

The reference compound was phentolamine and the positive control was prazosin. The assay was characterized by a $K_i$ of 0.2 nM, a $B_{max}$ of 95 fmol/g wet weight of tissue, and 95% non-specific binding as determined $3 \times 10^{-7}$ M prazosin.

The values for binding affinity of the reference compounds for the alpha1-adrenergic receptor are provided in Table IV.

TABLE IV

| Compounds | $K_i$ (nM) |
| --- | --- |
| Prazosin | 0.3 |
| WB4101 | 2.6 |
| Phentolamine | 13 |
| Yohimbine | 79.3 |

The values for alpha1-adrenergic receptor binding affinities for the compositions of this invention are provided in Table III. These results show that trans-9, trans-(+)-9, trans-25, trans-(+)-25, trans-(-)-25, cis-25, and trans-31 demonstrated high binding affinities for the α1 receptor.

EXAMPLE 18

Alpha2-Adrenergic (Non-Selective) Binding Assay

Alpha2-adrenergic binding assays were performed on rat cortical membranes according to the method described by Doxy, et al., *British Journal of Pharmacology*, 80:155–161 (1983). Incubation was conducted in 50 mM TRIS-HCl (pH 7.4) at 0° C. for 90 minutes. The radioligand used was [$^3$H]RX 781094 (40–60 Cl/mmol). The final ligand concentration was 1.5 nM.

The reference compound was phentolamine and the positive control was clonidine. The assay was characterized by a $K_i$ of 0.5 nM, a $B_{max}$ of 142.7 fmol/g wet weight of tissue, and 90% non-specific binding as determined using 10 μM phentolamine.

The value for binding affinity of the reference compounds for the alpha2-adrenergic receptor are provided in Table V.

TABLE V

| Compounds | $K_i$ (nM) |
| --- | --- |
| Phentolamine | 1.7 |
| Clonidine | 14 |
| Yohimbine | 24 |
| Prazosin | 29 |
| Rauwolscine | 40 |

The values for alpha2-adrenergic receptor binding affinities for the compositions of this invention are provided in Table III. These results show that trans-9, trans-(-)-9, cis-9, cis-(-)-9, trans-25, trans-(-)-25, cis-25, trans-33 and trans-31 demonstrated high binding affinities for the α2 receptor.

EXAMPLE 19

Beta-Adrenergic (Non-Selective) Binding Assay

Beta-adrenergic binding assays were performed on rat cortical membranes according to the method described by Marco, et al., *Molecular Pharmacology*, 36:201–210 (1989). Incubation was conducted in 50 mM TRIS-HCl (pH 7.4) at 37° C. for 30 minutes. The radioligand used was [$^3$H]DHA (90–120 Ci/mmol). The final ligand concentration was 2.0 nM.

The reference compound and positive control was alprenolol. The assay was characterized by a $K_i$ of 1.74 nM, a $B_{max}$ of 2.33 fmol/g wet weight of tissue, and 70% non-specific binding as determined using $10^{-4}$ M alprenolol.

The values for binding affinity of the reference compounds for the beta-adrenergic receptor are provided in Table VI.

TABLE VI

| Compounds | $K_i$ (nM) |
| --- | --- |
| Pindolol | 1.1 |
| Alprenolol | 3.5 |
| Metoprotol | 45 |
| Isoproterenol | 80 |
| Albuterol | 2,880 |

The values for beta-adrenergic receptor binding affinities for the compositions of this invention are provided in Table III. These results show that none of the compositions of this invention had significant binding affinity for the β-adrenergic receptor.

EXAMPLE 20

Serotonin (5HT1) Binding Assay

Serotonin ($5HT_1$) binding assays were performed on rat cortical membranes according to the method described by Bennett et al., *Molecular Pharmacology*, 12:373–389 (1976). Incubation was conducted in 50 mM TRIS-HCl (pH 7.4) at 45 minutes for 37° C. The radioligand used was [$^3$H]Hydroxytryptamine binoxalate (15–30 Ci/mmol). The final ligand concentration was 3.0 nM.

The reference compound was serotonin and the positive control was LSD. The assay was characterized by a $K_i$ of 2.8 nM, a $B_{max}$ of 9.2 fmol/g wet weight of tissue, and 60% non-specific binding as determined using 10 μM serotonin.

The values for binding affinity of the reference compounds for the serotonin receptor are provided in Table VII.

TABLE VII

| Compounds | Ki (nM) |
| --- | --- |
| Serotonin | 4.6 |
| 5-Methoxytryptamine | 45.8 |
| Methlylsergide | 790 |
| CGS-120668 | 1,055 |

The values for serotonin receptor binding affinities for the compositions of this invention are provided in Table III. These results show that trans-9 and trans-(-)-25 demonstrated high binding affinity for the 5HT1 serotonin receptor.

EXAMPLE 21

Serotonin (5HT1A) Binding Assay

Serotonin (5HT1A) binding assays were performed on bovine hippocampus according to the method described by Hall et al., *Journal of Neurochemistry*, 44:1685–1696 (1985). Incubation was conducted at 10 minutes for 37° C. The radioligand used was [$^3$H]-8-OH-DPAT (>100 Ci/mmol). The final ligand concentration was 1.0 nM.

The reference compound was 8-OH-DPAT and the positive control was serotonin. The assay was characterized by a $K_i$ of 2. nM, a $B_{max}$ of 1626 fmol/g wet weight of tissue, and 90% non-specific binding as determined [10 μM serotonin].

The values for binding affinity of the reference compounds for the serotonin receptor are provided in Table VIII.

TABLE VIII

| Compounds | $K_i$ (nM) |
|---|---|
| 8-OH-DPAT | 1.4 |
| RU 24969 | 10.0 |
| Ketanserin | >10,000.0 |

The values for serotonin receptor binding affinities for the compositions of this invention are provided in Table III. These results show that trans-(-)-9, trans-(-)-25, trans-31 and trans-33 demonstrated high binding affinities for the 5HT1A serotonin receptor.

EXAMPLE 22

Serotonin (5HT2) Binding Assay

Serotonin (5HT2) binding assays were performed on rat cortical membranes according to the method described by Leysen, et al., *Molecular Pharmacology*, 21:301–314 (1982). Incubation was conducted in 50 mM TRIS-HCl (pH 7.5) at 36° C.) for 15 minutes. The radioligand used was [$^3$H]Ketanserin (60–90 Ci/mmol). The final ligand concentration was 1.0 nM.

The reference compound and positive control was methysergide. The assay was characterized by a $K_i$ of 0.43 nM, a $B_{max}$ of 30.9 fmol/g wet weight of tissue, and 65% non-specific binding as determined using 10 μM methysergide.

The values for binding affinity of the reference compounds for the serotonin receptor are provided in Table IX.

TABLE IX

| Compounds | $K_i$ (nM) |
|---|---|
| Ketanserin | 0.4 |
| Methysergide | 1.5 |
| D-LSD | 2.1 |
| Serotonin | 531.0 |

The values for serotonin receptor binding affinities for the compositions of this invention are provided in Table III. These results show that trans-(-)-9, trans-25, trans-(+)-25, trans-31 and (-)-trans-33 demonstrated high binding affinities for the 5HT2 serotonin receptor.

EXAMPLE 23

Serotonin (5HT3) Binding Assay

Serotonin (5HT3) binding assays were performed on NIE-115 neuroblastoma cells according to the method described by Lummis, et al., *European Journal Pharmacology*, 189:223–227 (1990). Incubation was conducted in 20 mM HEPES (pH 7.4) containing 150 mM NaCl at 25° C. for 30 minutes. The radioligand used was [$^3$H] GR65630 (30–50 Ci/mmol). The final ligand concentration was 0.7 nM.

The reference compound and positive control was MDL-72222. The assay was characterized by a $K_i$ of 0.3 nM, a $B_{max}$ of 233 fmol/108 cells, and 80–90% non-specific binding as determined using 1 μM MDL-72222.

The values for binding affinity of the reference compounds for the serotonin receptor are provided in Table X.

TABLE X

| Compounds | $K_i$ (nM) |
|---|---|
| Quipazin | 1.5 |
| MDL-72222 | 7.2 |
| Serotonin | 18.7 |
| Metoclopramide | 191.0 |

The values for serotonin receptor binding affinities for the compositions of this invention are provided in Table III. These results show that none of the compositions of this invention had significant binding affinity for the 5HT3 serotonin receptor.

Locomotor Activity Testing

Compounds of this invention were tested to evaluate any depressant effect upon locomotor activity on non-habituated and cocaine-influenced mice. Locomotor activity was measured in photocell cages. A panel of infrared beams was located in the horizontal direction along all 4 sides of each activity cage. Horizontal photocell beam interruptions were recorded by a computer in 10 minute intervals.

EXAMPLE 24

Locomotor Dose-Effect Tests

Non-habituated male Swiss-Webster served as subjects in this experiment. The mice were injected via the intraperitoneal (IP) route with a methycellulose vehicle or a test compound, comprising trans-9 or cis-9, and placed singly in cages for 20 minutes. After this 20 minute period, mice were injected with saline IP, placed in individual photocell cages and testing for effects upon locomotor activity was begun. Eight mice were tested at each dose level. Experimental sessions were 60 minutes in duration with horizontal locomotor activity recorded in 10 minute intervals. Within each 10 minute interval, the data from all subjects are averaged.

Figure 1A:
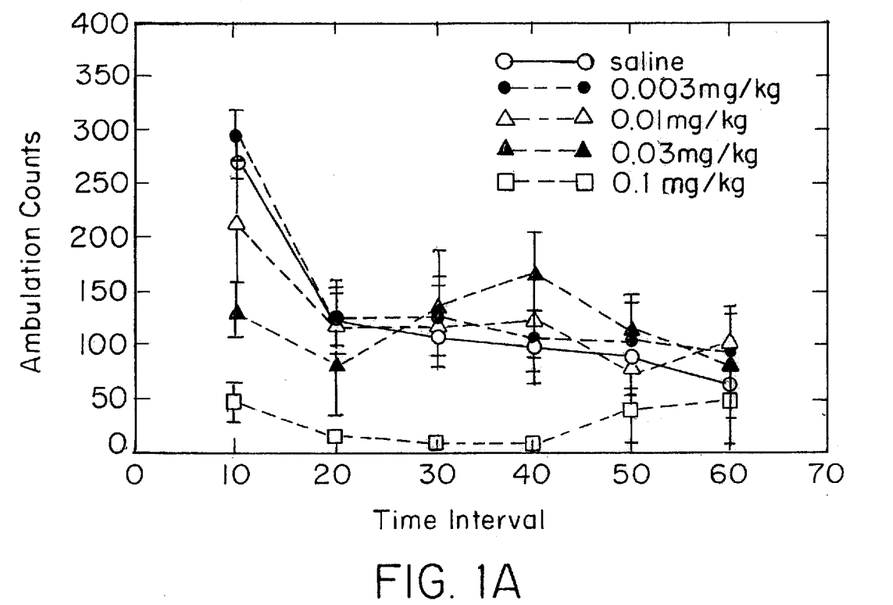
FIGS. 1a and 1b are plots of (a) the horizontal activity counts per 10 minute interval, and (b) the average horizontal activity counts per 10 minute period averaged over the first 30 minutes of the test, for mice treated with 0.003 mg/kg, 0.01 mg/kg, 0.03 mg/kg or 0.1 mg/kg doses of (±)-trans-7,8-dihydroxy-4-phenethyl-1,2,3,4a,5,6,10b-octahydrobenzo[f]quinoline or with a saline control.
Figure 1B:
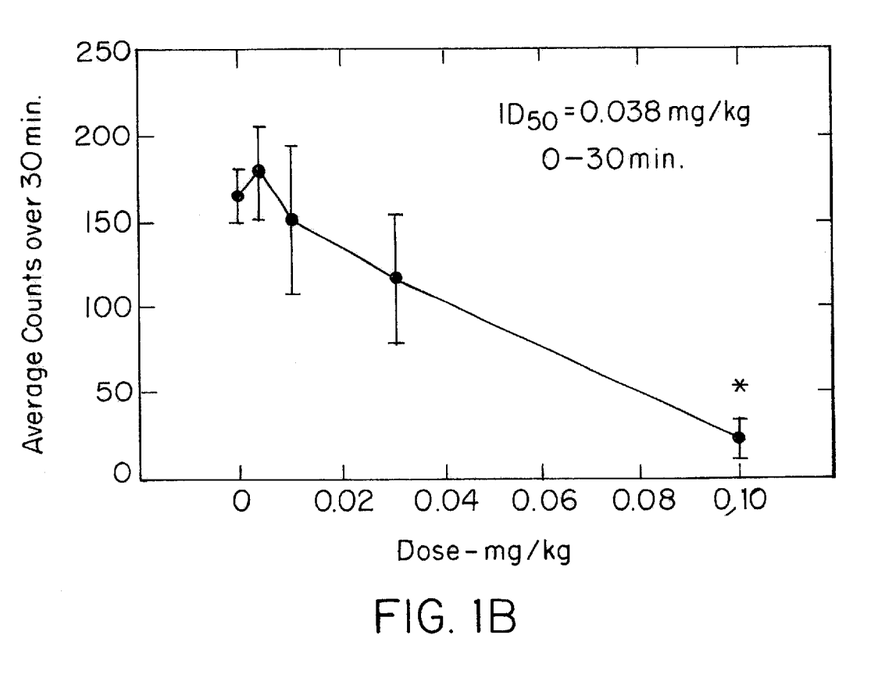
Figure 2A:
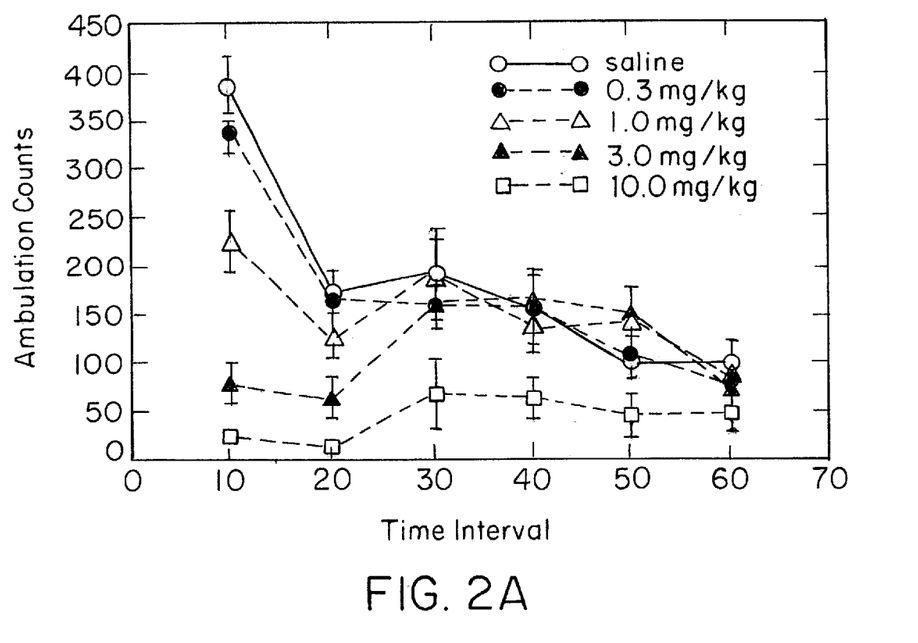
FIGS. 2a and 2b are plots of (a) the horizontal activity counts per 10 minute interval, and (b) the average horizontal activity counts per 10 minute period averaged over the first 30 minutes of the test, for mice treated with 0.3 mg/kg, 1.0 mg/kg, 3.0 mg/kg or 10.0 mg/kg doses of (±)-cis-7,8-dihydroxy-4-phenethyl-1,2,3,4a,5,6,10b-octahydrobenzo[f]quinoline or with a saline control.
Figure 2B:
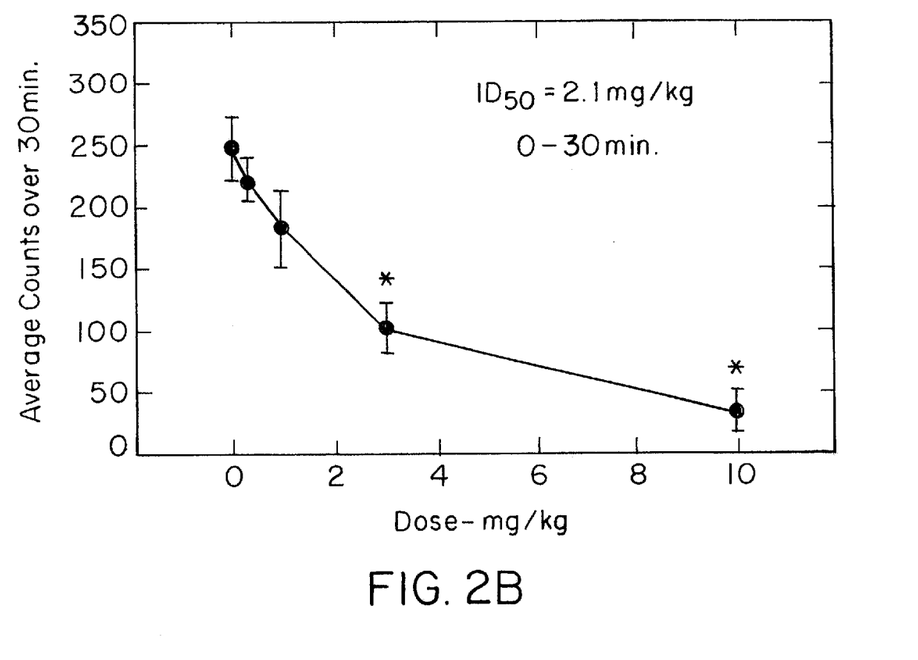

The results of these tests were provided in FIGS. 1a, 1b, 2a and 2b, as well as in Table XI. FIG. 1a shows an average horizontal activity counts for each successive 10 minute time period for the different doses of the compounds tested. FIG. 1b shows the average horizontal activity counts per 10 minute period during the first 30 minutes of the test session. Data were analyzed by a one-way ANOVA computed across doses using a $\log_{10}$ transformation of the horizontal activity counts. Comparisons between vehicle and each dose of the compounds tested were made by a priori contrasts. Doses of the compounds tested, which produced a statistically significant ($p<0.05$) decrease in locomotor activity relative to vehicle control, are denoted with an asterisk. The dose which produced 50% maximal depressant activity (hereinafter "$ED_{50}$") was determined by linear regression analysis of the dose-effect curve. The horizontal activity counts were regressed against the $\log_{10}$ dose of the test compound.

These tests indicate that trans-9 appears to be a strong agonist in inducing a decrease in locomotor activity in mice. Trans-9 showed marked suppression of locomotor activity when initially tested at 10 mg/kg. Marked suppression was still evident at 0.1 mg/kg in the first dose-response experiment, as shown in FIG. 1a). Lower doses were then evaluated with the results shown in FIGS. 2a and 3a.

Cis-9 was much weaker than expected when compared to its dopamine D2 receptor affinity. Cis-9 caused dose-related suppression of locomotor activity of 10 mg/kg. Two of eight mice died at 10 mg/kg.

TABLE XI

| COMPOUND | $ED_{50}$ (mg/kg) |
|---|---|
| trans-9 | 0.038 |
| cis-9 | 2.1 |

EXAMPLE 25

Sterotypy Evaluation for Dopaminergic Activity

Young, adult, male Sprague-Dawley (Charles River) albino rats (200–250 g) served as subjects in this experiment. The rats were injected IP with each dose of (±)-trans-9 or (±)-cis-9. Six rats were tested at each dose. Experimental sessions were 60 minutes in duration. The tests were performed and rated in accordance with the method described in Campbell et al., *Psychopharmacology*, 88:158 (1986). Each rat was rated with a score of 0 to 3, where 0 represents no sterotypy. The results of these tests are provided in Table XII.

These tests indicate that (±)-trans-9 appears to be a strong agonist as it induced stereotypy in rats while (±)-cis-9 did not induce stereotypy and therefore is not a dopamine agonist.

TABLE XII

| Dose (mg/kg) | trans-9 | cis-9 |
|---|---|---|
| 0.0 | 0.0 | 0.7 ± 0.3 |
| 0.0001 | 6.5 ± 0.4 | 1.0 ± 0.4 |
| 0.001 | 10.0 ± 0.9 | 0.7 ± 0.3 |
| 0.003 | 8.2 ± 0.8 | 0.5 ± 0.2 |
| 0.01 | 7.2 ± 0.6 | 0.0 |
| 0.03 | 6.5 ± 0.5 | 0.0 |
| 0.1 | 6.0 ± 0.7 | 0.0 |
| 0.3 | 1.7 ± 0.5 | 0.0 |
| 1.0 | 0.3 ± 0.2 | 0.0 |
| 3.0 | 0.2 ± 0.2 | 0.0 |
| 10.0 | 0.0 | 0.0 |

EXAMPLE 26

D2:D3:D4 Competition Binding Assay

To determine the D2, D3 or D4 receptor selectivity, competition binding assays were performed using membranes from fibroblast cell lines transfected with D2444 (rat), D3 (human) or D4 (rat) receptors. All cell lines were maintained in Dulbecco's modified Eagle's media (DMEM) supplemented with 10 % fetal bovine serum at 37° C. with 5% $CO_2$. Transfected cells were maintained in DMEM containing 300 μg/mL of the antibiotic G418 (Gibco).

Membranes were prepared from the cell lines and the assays were performed as described in Tang et al. *Journal of Pharmacology and Experimental Therapeutics* (in press 1933). Briefly, nearly confluent cells were harvested by scraping, washed twice in phosphate-buffered saline (PBS; 145 mM NaCl, 5 mM KCl, 0.7 mM $CaCl_2$, 0.5 mM $MgCl_2$, 10 mM phosphate, pH 7.4), resuspended in distilled water and homogenized with a Brinkman Polytron. Nuclei were removed by centrifugation for five minutes at 600 g at 4° C., membranes were pelleted for 25 minutes at 50,000 g. Membrane protein was resuspended in homogenization buffer (0.32M sucrose, 0.0025M Tris, pH 6.9 at 20° C.) and incubated at 37° C. for 15 minutes. Membrane protein was pelleted, resuspended in water and stored at –70° C.

Competition binding assays were done using 70–180 μg membrane protein and 2 nM [$^3$H]-spiperone (New England Nuclear, Boston, Mass.) in a final buffer of 5 mM EDTA, 1.5 mM $CaCl_2$, 5 mM $MgCl_2$, 5 mM KCl, 120 mM NaCl and 50 mM Tris-HCl (pH 7.4 at 20° C.). The compositions were tested in varying concentrations between 1 nM and 100 μM. Non-specific binding was determined using 1 μM eticlopride.

After addition of all components, the samples were incubated for 15 minutes at 37° C., terminated with 50 mM Tris-HCl (pH 7.4 at 4° C.) and collected on glass-fiber filters on a Brandel cell harvester. Radioactivity retained on the filters was counted on a Beckman LS 1701 scintillation counter and data were analyzed by non-linear least squares regression methods. The results of these tests are provided in Table XIII. Each composition was evaluated in duplicate experiments.

These tests indicate that cis-(±)-9 is highly selective for the D4 receptor over the D2 or D3 receptors. The tests also indicate that trans-(±)-9 is highly selective for the D3 receptor over the D2 or D4 receptors.

TABLE XIII

| COMPOUND | D2 | D3 | D4 |
|---|---|---|---|
| trans-25 | 1.640(±0.51)E–7 | 3.882(±2.39)E–7 | 1.352(±0.44)E–7 |
| trans-25 | 2.920(±0.38)E–7 | 7.547(±3.86)E–7 | 9.550(±4.24)E–7 |
| cis-25 | 3.659(±0.93)E–8 | 2.923(±0.58)E–8 | 5.217(±3.43)E–8 |
| cis-25 | 3.252(±1.34)E–8 | 1.590(±2.20)E–8 | 5.723(±4.37)E–8 |
| trans-9 | 1.048(±0.29)E–7 | 3.148(±2.45)E–9 | 7.412(±1.91)E–8 |
| trans-9 | 3.998(±3.75)E–7 | 3.302(±2.17)E–9 | 8.626(±3.35)E–8 |
| cis-9 | 4.734(±3.13)E–7 | 2.084(±1.21)E–7 | 3.788(±2.65)E–9 |
| cis-9 | 8.852(±4.26)E–7 | 5.609(±0.74)E–7 | 1.188(±0.63)E–9 |

EXAMPLE 27

D2:D4 Comparative Binding Assay

To evaluate D2 versus D4 receptor selectivity, comparative binding assays were performed to compare the binding affinities of compositions of this invention for cloned D2 and D4 receptors.

The D2 assay was prepared from pig anterior pituitary tissue as described in Seeman et al., *Molecular Pharmacology*, 28:391 (1985). The D4 assay contained membranes prepared from COS-7 cells transfected with a 3.9 kb cDNA-gene fusion construct as described in H. H. M. Vantol, *Nature*, 350:610 (1991).

Binding assays were done using the methods described in by Seeman and Vantol. [$^3$H]-spiperone (New England Nuclear, Boston, Mass.). The compositions were tested varying concentrations.

After addition of all components, the samples were incubated for 15 minutes at 37° C., terminated with 50 mM Tris-HCl (pH 7.4 at 20° C.) and collected on glass-fiber filters on a Brandel cell harvester. Radioactivity retained on the filters was counted on a Beckman LS 1701 scintillation counter and data were analyzed by non-linear least squares regression methods. The receptor binding results ($K_i$ in nM) of these tests are provided in Table XIV.

These tests indicate that cis-9 is selective for the D4 receptor over the D2 or D3 receptors.

TABLE XIV

| Compound | D2 (pig anterior pituitary) | D4 (Cos 7 cell) |
|---|---|---|
| trans-9 | 6.9 | 2.4 |
| cis-9 | 122 | 8.9 |

EXAMPLE 28

D2 Receptor Agonist Evaluation

To determine whether or not compounds of this invention were D2 receptor agonists, a membrane binding assay, utilizing the D2 cell line described in Example 26, was performed in the presence and absence of the non-hydrolyzable guanine nucleotide (GTP analogue) Gpp(NH)p. A shift in $K_i$ (nM) with Gpp(NH)p would be indicative of G-protein coupling and would therefor suggest the compound was an agonist. The effects of GTP on receptor binding (nM) of these tests are provided in Table XV.

These tests indicate that trans-9 and trans-25 appear to be agonists as D2 receptor binding was enhanced by the addition of GTP, while cis-9 and cis-25 appear to be an antagonist as the addition of GTP did not significantly affect receptor binding affinity.

TABLE XV

| Compound | with Gpp(NH)p | without Gpp(NH)p | Ratio of +:− |
|---|---|---|---|
| trans-9 | 924 ± 1840 | 105 ± 29 | 8.82 |
| cis-9 | 872 ± 610 | 473 ± 313 | 1.84 |
| trans-25 | 1270 ± 1640 | 37 ± 9 | 34.7 |
| cis-25 | 176 ± 213 | 164 ± 51 | 1.07 |

Equivalents

Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A pharmaceutical composition having anti-psychotic activity, comprising a pharmaceutically acceptable carrier and an effective amount of the cis stereoisomer of a compound represented by the formula:

wherein:

$R^1$ is —OH or —OCH$_3$;

$R^2$ is —H, —OH or —OCH$_3$;

$R^3$ is a C2 to C4 alkyl group; and $R^4$ is an aryl group.

2. An anti-psychotic pharmaceutical compositions of claim 1 wherein said compound is cis-7,8-dihydroxy-4-phenethyl-1,2,3,4,4a,5,6,10b-octahydrobenzo[f]quinoline.

3. A pharmaceutical composition having sedative activity, comprising a pharmaceutically acceptable carrier and an effective amount of cis stereoisomer of a compound represented by the formula wherein:

$R^1$ is —OH or —OCH$_3$;

$R^2$ is —H, —OH or —OCH$_3$;

$R^3$ is a C2 to C4 alkyl group; and $R^4$ is an aryl group.

4. A method of sedating a mammal, comprising administering to the mammal in need thereof stereoisomer of a compound represented by the formula:

wherein:

$R^1$ is —OH or —OCH$_3$;

$R^2$ is —H, —OH or —OCH$_3$;

$R^3$ is a C2 to C4 alkyl group; and $R^4$ is an aryl group.

5. The method of claim 4, wherein said compound is cis-7,8-dihydroxy-4-phenethyl-1,2,3,4,4a,5,6,10b-octahydrobenzo[f]quinoline.

6. A sedative composition of claim 3, further comprising an effective amount of cis-7,8-dihydroxy-4-phenethyl-1,2,3,4,4a,5,6,10b-octahydrobenzo[f]quinoline.

* * * * *